United States Patent [19]
Whiting et al.

[11] Patent Number: 5,054,045
[45] Date of Patent: Oct. 1, 1991

[54] CORONARY TRACKING DISPLAY

[75] Inventors: James S. Whiting; Neal Eigler, both of Los Angeles, Calif.

[73] Assignee: Cedars-Sinai Medical Center, Los Angeles, Calif.

[21] Appl. No.: 614,790

[22] Filed: Nov. 14, 1990

[51] Int. Cl.⁵ .................................................. H05G 1/64
[52] U.S. Cl. .......................................... 378/99; 358/111
[58] Field of Search ............................ 378/99; 358/111

[56] References Cited

U.S. PATENT DOCUMENTS 4,674,107 6/1987 Urban et al. ........................... 378/99

Primary Examiner—Craig E. Church
Attorney, Agent, or Firm—Lyon & Lyon

[57] ABSTRACT

A method of displaying details of a coronary artery lesion in a cineangiogram, by digitally adjusting each frame of the cineangiogram so that the lesion is continually displayed at a fixed location on a display screen. The remaining cardiac anatomy appears to move, in background, past a stationary arterial segment, thus making the displayed arterial segment easier to identify and to examine by medical personnel. Cineangiographic image frames are digitized and processed by an image processor and the image frames are digitally shifted to place the arterial segment in substantially the same viewing location in each frame. Sequential image frames may be presented to the viewer as a stereoscopic pair, to produce pseudostereopsis. The arterial segment appears to the viewer in foreground, as if it was floating in front of the remaining cardiac anatomy. Image frames may be further processed to aid examination by medical personnel. Frames may be averaged to reduce quantum noise and to blur any structure noise. Frame averaging may be used to make numerical measurements of arterial cross-section.

16 Claims, 1 Drawing Sheet

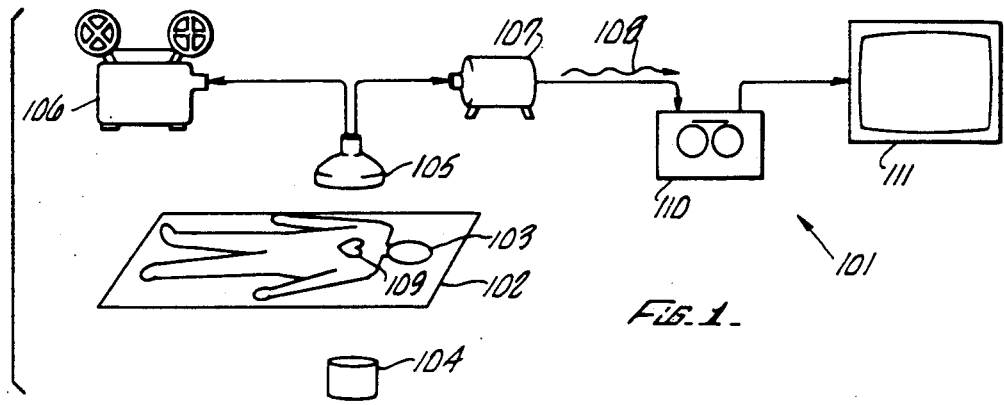
Fig. 1
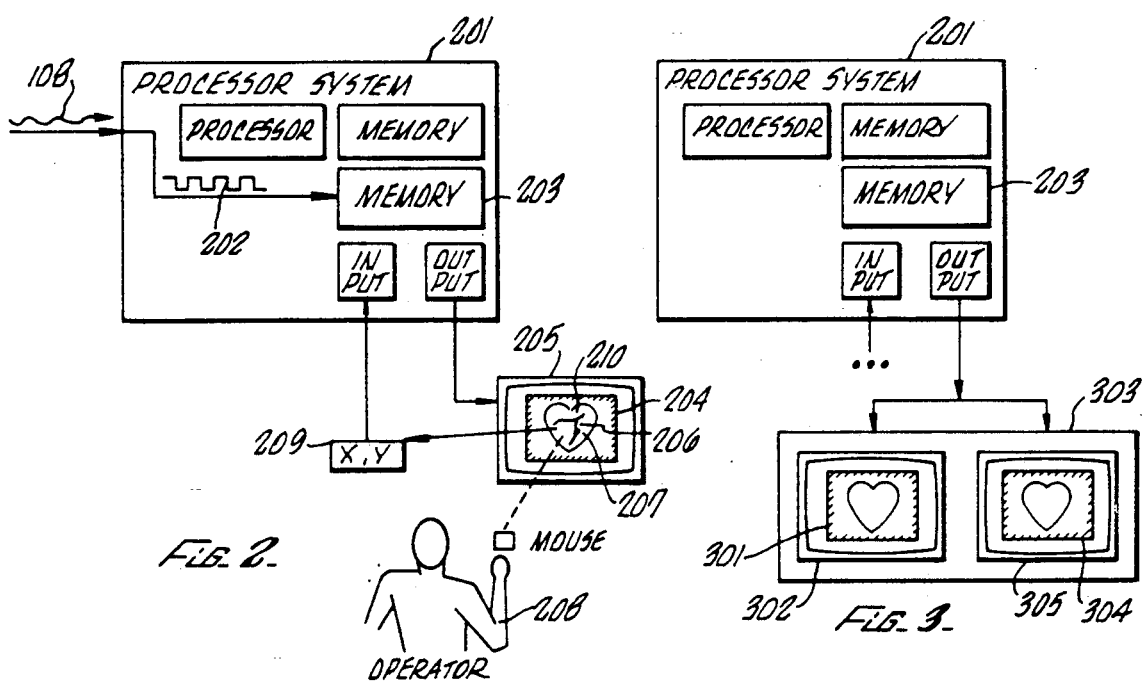
Fig. 2
Fig. 3
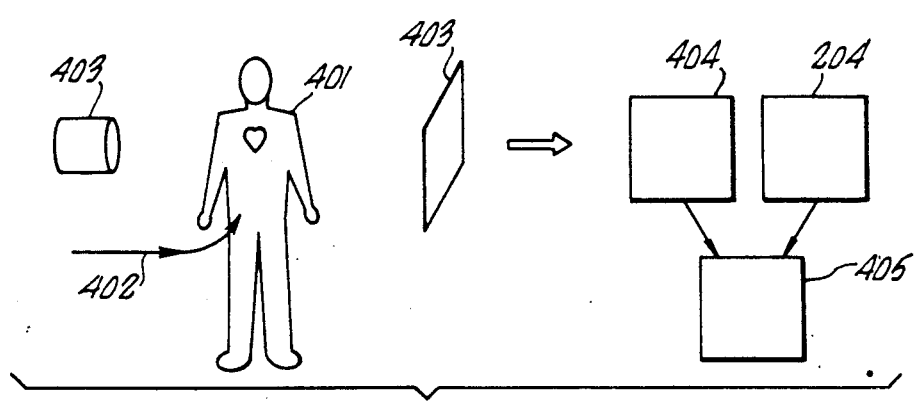
Fig. 4

CORONARY TRACKING DISPLAY

BACKGROUND OF THE INVENTION

1. Field of the Invention

This invention relates to a coronary tracking display. More specifically, this invention relates to a coronary tracking display which improves visibility of details of coronary artery lesions in cineangiography.

2. Description of Related Art

Cineangiography for coronary arterial segments is typically done by means of an x-ray image. An artery is filled with a contrast material (for example, a large molecule with iodine in it, such as megluamine diatrozoate (sold under the name Renografin 76) or iohexal (sold under the name Omnipaque), and its arterial segments are examined. Medical personnel may examine the shape of the inner wall of the artery and look for space where the contrast material would be expected to fill, but does not. These spaces are called "filling defects" and commonly indicate lesions for which a specific treatment may be desireable.

It is advantageous to collect and display images of coronary arterial segments for later review by medical personnel. For example, review of such images may prove useful in detecting and locating lesions, and thus may assist in treatment of a patient by interventional methods. However, one problem which has arisen in the art is that image quality under conditions imposed by cineangiography may be poor, making it difficult for medical personnel to readily recognize critical features.

It may also be advantageous to insert a catheter into an artery, approach an arterial segment containing a lesion, and perform an interventional therapy on that lesion. For example, a lesion may be dilated with a balloon or ablated with a laser. Because these treatments may have adverse effects, it is desireable to identify which lesions truly require treatment.

Another problem which has arisen in the art is that it may be difficult to move such a catheter within the patient's arterial network. It would be advantageous to superimpose an image of the catheter on the patient's arterial network while moving the catheter. However, the contrast material may have adverse effects on the patient, so it is generally not preferred to collect and display cineangiographic images while moving a catheter.

SUMMARY OF THE INVENTION

The invention provides a method of displaying details of a coronary artery lesion in a cineangiogram, by digitally adjusting each frame of the cineangiogram so that the lesion is continually displayed at a fixed location on a display screen. As a result, the remaining cardiac anatomy appears to move, in background, past a stationary arterial segment, thus making the displayed arterial segment easier to identify and to examine by medical personnel. In a preferred embodiment, cineangiographic image frames are digitized and processed by a processor and the image frames are digitally shifted to place the arterial segment in substantially the same viewing location in each frame.

In a preferred embodiment, sequential image frames may be presented to the viewer as a stereoscopic pair, to produce pseudostereopsis. As a result, the arterial segment appears to the viewer in foreground, as if it was floating in front of the remaining cardiac anatomy. Moreover, image frames may be further processed to aid examination by medical personnel. For example, frames may be averaged to reduce quantum noise and to blur any structure noise. In a preferred embodiment, frame averaging may be used to make numerical measurements of arterial cross-section.

BRIEF DESCRIPTION OF THE DRAWINGS

FIG. 1 shows a drawing of a cineangiographic system.

FIG. 2 shows a block diagram of a digital processing system for adjusting the image of the lesion in a cineangiogram.

FIG. 3 shows a block diagram of a digital processing system for producing pseudostereopsis.

FIG. 4 shows a block diagram and drawing of a cineangiographic system being employed to aid in catheterization.

DESCRIPTION OF THE PREFERRED EMBODIMENT

FIG. 1 shows a drawing of a cineangiographic system.

A cineangiographic system 101 may comprise a table 102 on which a patient 103 is placed, with an x-ray generating tube 104 below the table 102 for projecting x-rays and an x-ray intensifier tube 105 placed above the table for receiving x-rays. The x-ray intensifier tube 105 may be coupled to a motion-picture camera 106 or a television camera 107, which may produce a video image signal 108 of the patient's heart 109, as is well known in the art. The video image signal 108 may be stored on a storage medium such as a videotape 110, and may later be retrieved and displayed on a video monitor 111 for review by medical personnel, as is well known in the art.

FIG. 2 shows a block diagram of a digital processing system for adjusting the image of the lesion in a cineangiogram.

In a preferred embodiment, the video image signal 108 may be coupled to a processor system 201, which may digitize the video image signal 108 and store a digital signal 202 in a memory 203. The processor system 201 may then adjust each frame of the cineangiogram so that a lesion is continually displayed at a fixed location on a display screen.

In a preferred embodiment, the processor system 201 may comprise a processor, memory comprising a stored program, memory comprising data, and input/output devices, as is well known in the art. Although the operation of the processor system 201 is given in terms of functions that it performs, it would be clear to one of ordinary skill in the art, after perusal of the specification, drawings and claims herein, that modification and/or programming of a standard microprocessor to achieve the functions disclosed herein would be a straightforward task and would not require undue experimentation.

In a preferred embodiment, the processor system 201 may comprise an ADAC computer made by ADAC Corporation, or may be a GE DXC image acquisition system made by General Electric Corporation.

Collecting Data on Lesion Location

In a preferred embodiment, the processor system 201 may operate interactively with a human operator, as is well known in the art. First, the processor system 201 may retrieve a single frame 204 of the stored digital signal 202 from memory 203, and may display that frame 204 on an operator's monitor 205. As each frame 204 is displayed, the cineangiogram will show a motion picture of the patient's heart 109. In this motion picture, an arterial segment 206 may appear on which there is a lesion 207. However, because of the patient's heartbeat, the lesion 207 will tend to move about on the screen.

A human operator 208 may examine the operator's monitor 205 and may indicate (e.g., with a pointing device such as a light pen, mouse or trackball) the location in the frame 204 of the lesion 207. The processor system 201 may receive the indication by the operator 208 and may store a set of spatial coordinates 209 for the lesion 207 which it associates with the frame 204. The processor system 201 may then repeat this interactive process for each frame 204 of the stored digital signal 202. When complete, the processor system 201 will have a record stored in memory 203 of movements which the lesion 207 undergoes as a result of the patient's heartbeat.

In an alternative preferred embodiment, the processor system 201 may locate the lesion 207 by edge-detection or other automatic means. For example, the stored digital signal 202 may comprise a set of pixels, each of which represents a measure of light level detected by the television camera 107. The patient's arterial network may have a different light level from other structure. The processor system 201 may then trace the patient's arterial network and determine what areas of the digital signal 202 represent arteries and what areas represent other structure.

In a preferred embodiment, the technique used by the processor system 201 for edge-detection may comprise a technique based on an optimum matched filter, described in a technical appendix to this application and hereby incorporated by reference as if fully set forth herein. A description of a preferred optimum matched filter technique is also given in the Ph.D. thesis of J. Martin Pfaff, on file with the UCLA Library System, and hereby incorporated by reference as if fully set forth herein. However, it would be clear to one of ordinary skill in the art, after perusal of the specification, drawings and claims herein, that other techniques for edge-detection or for otherwise locating the lesion 207 would be workable, and are within the scope and spirit of the invention.

In one aspect of this alternative preferred embodiment, the operator 208 may identify the lesion 207 in one frame 204 by the same technique, but the processor system 201 may determine the location of the lesion 207 in the succeeding frames 204 automatically. For example, the processor system 201 may locate the lesion 207 by noting the distance from the lesion 207 to a reference point 210, such as a junction of arterial segments, and by locating the lesion 207 in the succeeding frames 204 by reference to the reference point 210.

In another aspect of this alternative preferred embodiment, the processor system 201 may determine the location of the lesion 207 by noting a point in the arterial segment where the arterial segment is much narrower. In this aspect, the operator 208 may identify the lesion 207 of interest out of several possible lesions 207 which might be displayed.

Displaying the Lesion

The processor system 201 may then display the stored digital signal 202 on the video monitor 111 for review by medical personnel. First, the processor system 201 may retrieve a single frame 204 from memory 203, and note the spatial coordinates 209 of the lesion 207. The processor system 201 may then adjust that frame 204 to place the lesion 207 in a specified location (e.g., a position near the center of the screen). Alternatively, the processor system 201 may adjust each frame 204 except the first to place the lesion 207 in the same location as in the first frame 204. As a result, the lesion 207 appears in the same location in each screen, and the remaining cardiac anatomy appears to move, in background, past a stationary arterial segment.

Pseudostereopsis

FIG. 3 shows a block diagram of a digital processing system for producing pseudostereopsis.

In a preferred embodiment, the processor system 201 may present a pair of sequential frames 204 to medical personnel as a stereoscopic pair, to produce pseudostereopsis. An odd frame 301 is displayed on a left half 302 of a stereoscopic display 303, while an even frame 304 is displayed on a right half 305 of the stereoscopic display 303. When the stereoscopic display 303 is viewed with appropriate stereoscopic equipment, a three-dimensional image will appear, as is well known in the art. As a result, the arterial segment appears to the viewer in foreground, as if it was floating in front of the remaining cardiac anatomy.

In a preferred embodiment, the processor system 201 may further process the frames 204 to aid examination by medical personnel. For example, the frames 204 may be averaged to reduce quantum noise and to blur any structure noise. In a preferred embodiment, the processor system 201 may use frame averaging to make numerical measurements of arterial cross-section.

Aid in Catheterization

FIG. 4 shows a block diagram and drawing of a cineangiographic system being employed to aid in catheterization.

In a preferred embodiment, a catheter patient 401 may be catheterized with a catheter 402 which is inserted into one of the patient's arteries (typically the femoral artery), as is well known in the art. In a preferred embodiment, the catheter patient 401 may be positioned on a fluoroscope 403, which generates an x-ray image 404 of the catheter 402. The x-ray image 404 may then be superimposed on a frame 204 retrieved from memory 203 by the processor system 201, to form a composite image 405. The composite image 405 may then be adjusted so that the catheter remains in the same location in the image.

For example, the processor system 201 may simply "play back" the set of coordinate adjustments it made for the cineangiogram, applying those same coordinate adjustments to the x-ray image 404 of the catheter 402. In this aspect of the invention, movement of the image which is due to the patient's heartbeat may be essentially eliminated, so that medical personnel performing the catheterization may determine routing of the catheter in the patient's arterial network.

It would be clear to one of ordinary skill in the art, after perusal of the specification, drawings and claims herein, that other and further signal processing may be performed on the stored digital signal 202, such as filtering, noise-removal and other related techniques. Such other and further signal processing would be workable, and is within the scope and spirit of the invention.

Alternative Embodiments

While preferred embodiments are disclosed herein, many variations are possible which remain within the concept and scope of the invention, and these variations would become clear to one of ordinary skill in the art after perusal of the specification, drawings and claims herein.

We claim:

1. A method of displaying a segment of a coronary artery in a cineangiogram, comprising the step of
   digitally adjusting each frame of the cineangiogram so that the segment is continually displayed at a substantially fixed location on a display screen.

2. A method of displaying a segment of a coronary artery in a cineangiogram, comprising the steps of
   digitizing cineangiogram image frames;
   locating an arterial segment in said image frames;
   digitally shifting said image frames to place the arterial segment in substantially the same viewing location in each one of said image frames.

3. A method as in claim 2, wherein said step of locating comprises the steps of
   displaying at least one of said image frames to an operator; and
   retrieving information indicating a location of said arterial segment from said operator.

4. A method as in claim 2, wherein said step of locating comprises the step of edge-detection.

5. A method as in claim 2, wherein sequential image frames are presented to a viewer as a stereoscopic pair.

6. A method as in claim 2, wherein image frames are further processed to aid examination by a viewer.

7. A method as in claim 2, comprising the step of averaging a plurality of said frames.

8. A method as in claim 7, comprising the step of computing a measure of vessel cross-section based on a result of said step of averaging.

9. A method of displaying a segment of a coronary artery in a cineangiogram, comprising the steps of
   identifying said segment in a plurality of frames of said cineangiogram;
   adjusting a display position of each of said frames so that said segment is placed in substantially the same viewing location in each of said frames.

10. A method of displaying a segment of a coronary artery in a cineangiogram, comprising the steps of
    identifying said segment in a plurality of frames of said cineangiogram;
    adjusting a display position of each of said frames so that said segment is placed in substantially the same viewing location in each of said frames; and
    displaying each of said frames in its adjusted display position.

11. A method as in claim 10, wherein said frames comprise digital image frames.

12. A method as in claim 10, wherein said step of identifying comprises the steps of
    displaying at least one of said image frames to an operator; and
    retrieving information indicating a location of said arterial segment from said operator.

13. A method as in claim 10, wherein said step of identifying comprises the step of edge-detection.

14. A method of moving a catheter in a patient, comprising the steps of
    producing an image of said catheter in said patient's body;
    adjusting a display position of each of said frames so that said image of said catheter is placed in substantially the same viewing location in each of said frames; and
    displaying each of said frames in its adjusted display position.

15. A method as in claim 14, wherein said image of said catheter is an x-ray image.

16. A method as in claim 14, wherein said step of adjusting the steps of
    determining a set of adjustments to be applied to a first plurality of frames, based on a location of an arterial segment in a second plurality of frames;
    applying said set of adjustments to said display position of said image of said catheter.

* * * * *

UNITED STATES PATENT AND TRADEMARK OFFICE
CERTIFICATE OF CORRECTION

PATENT NO. : 5,054,045

DATED : Oct. 1, 1991

INVENTOR(S) : WHITING, James S. et al.

It is certified that error appears in the above-identified patent and that said Letters Patent is hereby corrected as shown below:

Column 6, line 36, after "adjusting" insert -- comprises --.

Signed and Sealed this

Twelfth Day of July, 1994

Attest:

BRUCE LEHMAN

Attesting Officer

Commissioner of Patents and Trademarks

UNITED STATES PATENT AND TRADEMARK OFFICE
CERTIFICATE OF CORRECTION

| | | |
|---|---|---|
| PATENT NO. | : 5,054,045 | Page 1 of 1 |
| APPLICATION NO. | : 07/614790 | |
| DATED | : October 1, 1991 | |
| INVENTOR(S) | : Whiting et al. | |

It is certified that error appears in the above-identified patent and that said Letters Patent is hereby corrected as shown below:

In column 1, under the title of the invention, please insert the following:

--FEDERAL SUPPORT
The U.S. Government has a paid-up license in this invention and the right in limited circumstances to require the patent owner to license others on reasonable terms as provided for by the terms of Grant No. R01HL42997-01A1 awarded by the National Institutes of Health.--

Signed and Sealed this

Second Day of June, 2009

JOHN DOLL
*Acting Director of the United States Patent and Trademark Office*